US008728745B2

(12) United States Patent
Martin et al.

(10) Patent No.: US 8,728,745 B2
(45) Date of Patent: May 20, 2014

(54) METHOD FOR PREDICTION OF THE PROGRESSION RISK OF TUMORS

(75) Inventors: Peter Martin, Gaiberg (DE); Rüdiger Ridder, Schriesheim (DE)

(73) Assignee: Ventana Medical Sysems, Inc., Tucson, AZ (US)

( * ) Notice: Subject to any disclaimer, the term of this patent is extended or adjusted under 35 U.S.C. 154(b) by 311 days.

(21) Appl. No.: 13/062,185

(22) PCT Filed: Sep. 4, 2009

(86) PCT No.: PCT/EP2009/006415
§ 371 (c)(1),
(2), (4) Date: Mar. 18, 2011

(87) PCT Pub. No.: WO2010/025928
PCT Pub. Date: Mar. 11, 2010

(65) Prior Publication Data
US 2011/0183333 A1  Jul. 28, 2011

(30) Foreign Application Priority Data
Sep. 4, 2008  (EP) .................................... 08105235

(51) Int. Cl.
*G01N 33/574* (2006.01)
(52) U.S. Cl.
USPC ....................................................... 435/7.23
(58) Field of Classification Search
None
See application file for complete search history.

(56) References Cited

U.S. PATENT DOCUMENTS

| 7,422,859 | B2 | 9/2008 | Ridder et al. |
| 7,425,617 | B2 | 9/2008 | Beach et al. |
| 7,517,662 | B2 | 4/2009 | Ridder et al. |
| 8,367,353 | B2 | 2/2013 | Ridder et al. |
| 2009/0176204 | A1 | 7/2009 | Ridder et al. |
| 2009/0181406 | A1 | 7/2009 | Ridder et al. |

FOREIGN PATENT DOCUMENTS

| EP | 1507148 A1 | | 2/2005 |
| EP | 1 510 820 | * | 3/2005 |
| EP | 1510820 A1 | | 3/2005 |
| WO | WO 2004/038418 | * | 5/2004 |

OTHER PUBLICATIONS

Brunner et al (Pathobiology, 2008, 75:25-33).*
Santos et al (European Journal of Surgical Oncology, 2003, 29:74-80).*
Kruger et al (European Urology, 2005, 47:463-467).*
Myers (Histologic Technical Bulletin for Histotechnology, 2006, p. 25-29 of 48).*
Santos et al (European Journal of Surgical Oncology, 2003, 29:74-80).*
International Search Report, Dec. 18, 2009.
Klaes et al., "Overexpression of p16$^{INK4A}$ as a Specific Marker for Dysplastic and Neoplastic Epithelial Cells of the Cervix Uteri", International Journal of Cancer, vol. 92, pp. 276-284, 2001.
Abstract of: Prigge et al., "Human Papillomavirus Infection and p16$^{INK4A}$/KI-67 Co-Expression in the Head and Neck Squamous Epithelium", and Christensen et al., Eurogin 2011 Congress Abstracts Publication, pp. 204, May 2011.
Prigge, et al., "Association of HPV DNA Presence with p16$^{IN14A}$ Expression in Oropharyngeal Cancers Compared to Other Head and Neck Cancers, Dysplastic and Non-Dysplastic Head and Neck Squamous Epithelium", 28$^{th}$ International Papillomavirus Conference, San Juan, Puerto Rico, 2012.
Stepan et al., "P16, c-erbB2 and Ki67 Immunoexpression in Urothelial Carcinomas of the Bladder", Rom J Morphol Embryol, vol. 52, No. 2, pp. 653-658, 2011.
Piaton et al., "p16$^{INK4A}$/Ki-67 Dual Labelling as a Marker for the Presence of High-Grade Cancer Cells or Disease Progression in Urinary Cytopathology", Cytopathology, pp. 1-8, 2012.
Alameda et al., "Value of p16$^{INK4A}$ in the Diagnosis of Low-Grade Urothelial Carcinoma of the Urinary Bladder in Urinary Cytology", Cancer Cytopathology, pp. 276-282, published online Mar. 14, 2012 in Wiley Online Library (wileyonlinelibrary.com).

* cited by examiner

*Primary Examiner* — Laura B Goddard
(74) *Attorney, Agent, or Firm* — Perkins Coie LLP; Viola T. Kung

(57) ABSTRACT

The present invention concerns a method for predicting the potential for aggressive growth and/or the risk to progress to high grade cancer for tumors in cell based detection procedures. In one aspect the invention concerns the detection of overexpression of cyclin-dependent kinase inhibitor gene products as a tool for predicting the progression risk and/or potential for aggressive growth of tumors. In a second aspect the invention concerns predicting the progression risk and/or potential for aggressive growth in tumors on the basis of the simultaneous co-detection of the presence of overexpression of cyclin-dependent kinase inhibitor gene products together with the expression of markers for active cell proliferation. Further the invention concerns preparations of probes for diagnosis namely for predicting the progression risk and/or the potential for aggressive growth of tumors.

5 Claims, 1 Drawing Sheet

METHOD FOR PREDICTION OF THE PROGRESSION RISK OF TUMORS

This application is a National Stage of International Application PCT/EP2009/006415, filed Sep. 4, 2009, published Mar. 11, 2010, under PCT Article 21(2) in English; which claims the priority of European Patent Application No. 08105235.9, filed Sep. 4, 2008.

The present invention concerns a method for predicting the potential for aggressive growth and/or the risk to progress to high grade cancer for tumors in cell based detection procedures. In one aspect the invention concerns the detection of overexpression of cyclin-dependent kinase inhibitor gene products as a tool for predicting the progression risk and/or potential for aggressive growth of tumors. In a second aspect the invention concerns predicting the progression risk and/or potential for aggressive growth in tumors on the basis of the simultaneous co-detection of the presence of overexpression of cyclin-dependent kinase inhibitor gene products together with the expression of markers for active cell proliferation. Further the invention concerns preparations of probes for diagnosis namely for predicting the progression risk and/or the potential for aggressive growth of tumors.

BACKGROUND

Preventive programs have been offered for various cancers since the middle of the fifties. For certain cancers even population wide screening programs exist in various developed countries. Such screening programs are applicable for cancer entities and the respective precursor stages such as e.g. cervical cancer, cancers of the urinary system, of the respiratory tract and others.

In all cases of cancer screening the outcome of a diagnostic test is categorized in accordance with the severity of the detected lesion. Grading systems for categorizing cancers of different origins have been established and are widely used. In general for any cancer type low grade tumors can be found that are either benign or are mostly benign with a certain risk for progression to malignant growth.

Generally the detection of low grade lesions imposes problems to the diagnosing physician and on the patient. A moderate to high percentage of low grade lesions has the tendency to regress spontaneously without any further treatment necessary. On the other hand there is also a lower percentage of low grade lesions that will progress to more severe forms and will end up as invasive cancer. The dilemma with low grade lesions in practice is that it is hard to predict which particular lesion is prone to regress and which will progress to invasive cancer.

Several attempts have been made to predict the risk for progression and the potential for aggressive growth of low grade lesions. Especially molecular markers have been examined that might have the potential to predict progression. Especially the expression level of cell cycle regulation proteins has been checked and has been found to be helpful under certain circumstances.

Despite all attempts made so far there is a strong need for methods that allow predict the progression risk for tumors and especially for low grade cancerous lesions and cancer precursor lesions. Therefore, it is the object of the present invention to provide a method of predicting the progression risk of tumors.

The inventor found that detection of overexpression of cyclin-dependent kinase inhibitors may be used to predict the progression risk of tumors and also of early cancer precursor lesions. In addition the detection of a combination of cyclin-dependent kinase inhibitors and of cell proliferation markers may be used for prediction of the progression risk of tumors.

BRIEF DESCRIPTION OF THE INVENTION

It is one aspect of the present invention to provide a method for predicting the potential for aggressive growth and the risk to progress to high grade cancer for tumors comprising determining in a cell based detection procedure based on the detection of the presence of overexpression of cyclin-dependent kinase inhibitor gene products. In certain embodiments of the invention also the detection of specific staining patterns of overexpression in immuno-histochemistry may be applied in this method.

It is a second aspect of the present invention to provide a method for predicting the potential for aggressive growth and the risk to progress to high grade cancer for tumors comprising determining in a cell based detection procedure performed on the basis of the detection of the simultaneous presence of overexpression of at least one cyclin-dependent kinase inhibitor gene product and the expression of at least one cell proliferation marker gene product in at least one single cell.

It is a third aspect of the present invention to provide preparations of probes for diagnosis namely for predicting the progression risk and/or the potential for aggressive growth of tumors.

DETAILED DESCRIPTION OF THE INVENTION

Figure 1:
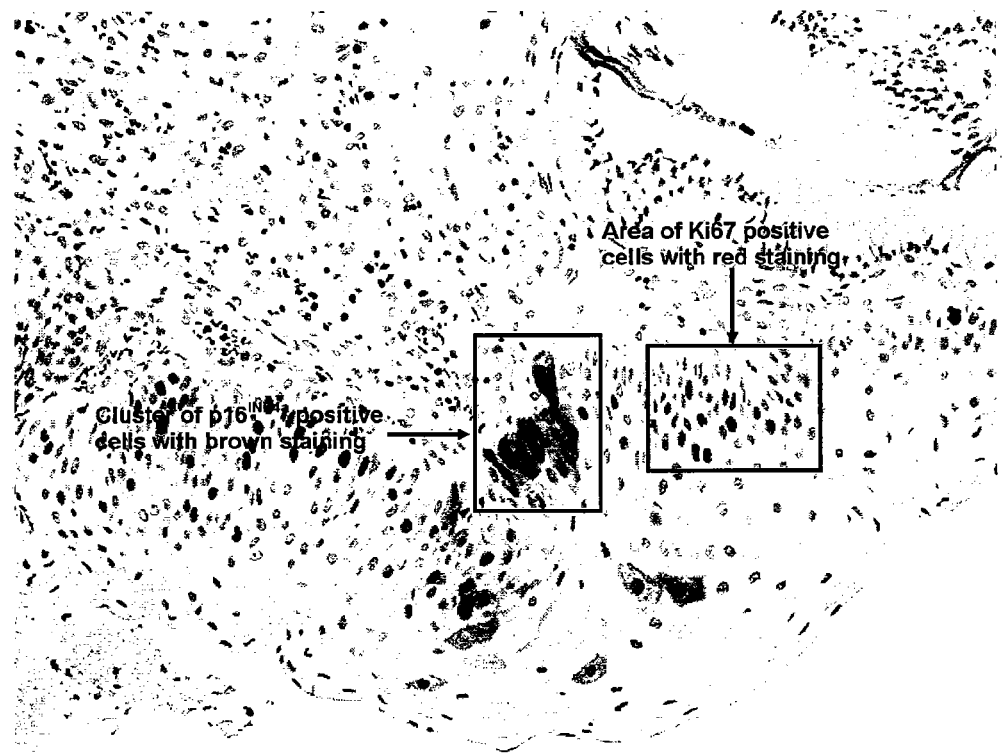
FIG. 1: Photomicrograph of a biopsy specimen from the cervix uteri immuno-histochemically double-stained using monoclonal antibodies directed to human $p16^{INK4a}$ protein and human Ki67 protein. Ki67 rendered specific red staining, $p16^{INK4a}$ specific brown staining. The staining pattern is focal for $p16^{INK4a}$. No cells double-stained for both markers are present.

During the experiments leading to the present invention the inventors came to the insight that detection of cyclin-dependent kinase inhibitors in tumors and also in early cancer precursor lesions or low grade cancers may be used for prediction of the potential for aggressive growth of cancers. Especially overexpression of cyclin-dependent kinase inhibitors concomitantly with expression of cell proliferation marker expression is an indication for progression to aggressive forms of cancer.

Further the inventors found that preparations of probes comprising a) at least one probe specific for a cyclin-dependent kinase inhibitor gene product and b) at least one probe specific for a cell proliferation marker gene product may be used for prediction of potential for aggressive growth and/or for prediction of progression risk in tumors and in early cancer precursor lesions and low grade cancers.

The denominations given throughout this text for genes may in part relate to the genes or proteins as they have been discovered from any organism. In the context of the present invention this denomination shall confer to the respective homologue of the named markers in the organism which is particularly in question for a method as disclosed herein. In certain embodiments of the present invention this organism is a mammal and in one embodiment may be a human being. Such in one embodiment of the present invention the named markers shall be the human homologues of the respective denominated ones.

A marker useful according to the present invention may be any molecule transcribed from a gene or any molecule translated from such a transcript. Thus "gene product" as used in the context of the present invention may comprise polynucleotides such as e.g. DNA or RNA and polypeptides such as proteins, proteoglycans, peptides etc.

"Cyclin-dependent kinase inhibitors" for use in the present invention comprise the cyclin-dependent kinase inhibitors $p14^{ARF}$, $p15^{INK4b}$, $p16^{INK4a}$, $p18^{INK4c}$, $p19^{INK4d}$, $p21^{WAF1/CIP1}$ and or $p27^{KIP1}$. Beside cyclin-dependent kinase inhibitors the cell cycle regulatory protein $p14^{ARF}$ encoded by an alternative reading frame of the $p16^{INK4a}$ gene may also be used for a method as disclosed herein. For convenience, within the context of the present invention the cell cycle regulatory protein $p14^{ARF}$, which is by function not a cyclin-dependent kinase inhibitor, shall be included in the expression "cyclin-dependent kinase inhibitor".

"p16" or "cyclin-dependent kinase inhibitor $p16^{INK4a}$" as used herein refers to cyclin-dependent kinase inhibitor $p16^{INK4a}$ (also denominated as CDKN2 or MTS1) the gene of which is located in chromosomal region 9p21. $p16^{INK4a}$ was first described in Serrano, M., et al., Nature, 1993 Dec. 16; 366(6456):704-7. The terms "$p16^{INK4a}$" or "cyclin-dependent kinase inhibitor $p16^{INK4a}$" in all their grammatical forms as used in the context of the present invention refers to nucleic acid as well as polypeptide molecules. "p16" or "cyclin-dependent kinase inhibitor $p16^{INK4a}$" thus comprises e.g. RNA (mRNA, hnRNA, etc.), DNA (cDNA, genomic DNA, etc.), proteins, polypeptides, proteoglycans, glycoproteins and the respective fragments of these molecules.

The term "(cell) proliferation marker" or "marker for cell proliferation" as used in the context of the present invention shall comprise any marker molecule known in the art to be characteristic for the proliferation status of cells. The proliferation status may e.g. be a status of actively proliferating cells, of retarded cell proliferation, of arrested cell proliferation, of senescent cells, of terminally differentiated cells, of apoptosis etc. In one embodiment of the invention the cell proliferation marker is a marker molecule characteristic for active cell proliferation. In another embodiment of the invention the proliferation marker molecule may be a molecule characteristic for arrested, terminally differentiated, senescent or apoptotic cells. Generally throughout the text the term "(cell) proliferation marker" or "marker for cell proliferation" in the various grammatical forms is used to denominate proteins as well as nucleic acid markers. In case the protein name of a marker such as e.g. "replication protein" is used herein, this use shall be understood to be metonymically and pertain as well to the protein as to the nucleic acid marker molecules encoding the particular protein In certain embodiments proliferation markers for use in the context of the present invention may comprise genes engaged in the DNA replication such as e.g. proteins of the pre-initiation complex or of the replication fork. Such molecules may e.g. comprise helicases, such as eucaryotic helicase or MCM proteins (MCM2, MCM3, MCM4, MCM5, MCM6, MCM7), protein TP as disclosed in WO0050451 and WO0217947 (also denominated HELAD1, Pomfil2, Unc-53), kinases or phosphatases engaged in the replication process such as e.g. CDC6, CDC7, CDC7 protein kinase, Dbf4, CDC14, CDC14 protein phosphatase, CDC45 and MCM10. Furthermore proliferation markers may comprise proteins engaged in the processive replication fork such as e.g. topoisomerases (e.g. topoisomerase2alpha) PCNA or DNA polymerase delta, replication protein A (RPA), replication factor C (RFC), FEN1.

In other embodiments the proliferation markers may comprise molecules necessary for the maintenance of cell proliferation such as Ki67. Ki-S5 or Ki-S2. In this embodiment proteins may be e.g. present throughout the whole cell cycle. They are useful for performing a method according to the present invention provided they are characteristic for active cell proliferation and are not significantly expressed in arrested, terminally differentiated, apoptotic or senescent states of cells. Ki67, Ki-S2 and Ki-S5 as used herein shall denominate the protein marker molecules detected by the respective antibodies as well as the nucleic acids encoding these antigens.

"Tumors" as used in the context of the present invention shall refer to any kind of tumor such as e.g. benign and malignant tumors, carcinomas, sarcomas, leukemias, lymhomas, carcinomas in situ, or dysplasias. Tumors may comprise tumors of the head and the neck, tumors of the respiratory tract, tumors of the gastrointestinal tract, tumors of the urinary system, tumors of the reproductive system, tumors of the endocrine system, tumors of the central and peripheral nervous system, tumors of the skin and its appendages, tumors of the soft tissues and bones, tumors of the lymphopoietic and hematopoietic system, breast cancer, colorectal cancer, anogenital cancer etc. The term "cancer" as used in the context of the present application shall refer to cancers of any kind and origin and precursor stages thereof, respectively. Accordingly the term "tumor" shall comprise the subject matter identified by the terms "neoplasia", "neoplasm", "cancer", "precancer", "carcinomas in situ", or "tumor". Also the cytological counterpart to histological conditions identified as "dysplastic" or as "dysplasia" shall be within the scope of the term "tumor" as used herein.

In certain embodiments of the present invention the term tumor shall refer to early stages of tumors and shall comprise especially tumors of Grades 1 (low grade) and 2 (intermediate grade) according to the classification of the UICC (Union Internationale Contre le Cancer). Especially Grade 1 comprising low grade tumors are of importance for the methods of the invention. Early stages of tumors shall also refer to tumors grades that correlate to the named UICC grade also in case the particular tumor is graded according to a different grading system. Especially for Breast cancer the terms "early cancer precursor lesions" as well as "early stages of tumors" shall comprise scores 3, 4 and 5 (low grade) and scores 6 and 7 (intermediate grade) of the Bloom-Richardson combined scores system. For Cervical cancer the terms "early cancer precursor lesions" as well as early stages of tumors shall comprise the categories LSIL and HSIL of the Bethesda Classification system, and CIN1, CIN2 and also CIN3 of the CIN Classification system. For cytological examinations and classification according to the munich classification system lesions classified as Pap I, Pap II, Pap II W and Pap III D shall be considered as "early cancer precursor lesions" as well as early stages of tumors.

Tumors to which the methods of the present invention may be applied comprise for example, neoplastic lesions of the respiratory tract, of the urinary system, of the gastrointestinal tract, of the anogenital tract, tumors associated with HPV infection and others. In one embodiment the HPV may be a high risk HPV subtype such as HPV16, HPV18, HPV31, HPV 33, HPV35, HPV 39, HPV 45, HPV 51, HPV 52, HPV56, HPV 58, HPV 59, HPV 66, and HPV 68. The tumors may be cancers of the respiratory tract, the urinary system, the reproductive tract or anogenital cancers, HPV associated cancers and particularly cervical cancer. In connection with the latter, its precursor stages, e.g. cervical intraepithelial neoplasias (CIN 1-3), carcinomas in situ (CIS), etc., have to be mentioned particularly. The term "precursor stages" in all its grammatical forms as used herein comprises all precursor stages and precursors of cancers or any other malignancies. With respect to cervical cancer precursor or preliminary stages as used herein may e.g. refer to stages of cervical intraepithelial neoplasias as identified by appropriate classification systems such as e.g. the CIN classification (CIN I-CIN III) the PAP classification (PAP I-PAP V) or the Bethesda Classification (NILM, LSIL, HSIL).

With respect to cancers of the respiratory tract cancers may comprise any malignant condition of the respiratory tract such as, e.g., cancer of the lung, the alveoles, the bronchioles, the bronchial tree and the broncus, the nasopharyngeal space, the oral cavity, the pharynx, the nasal cavity and the paranasal sinus. Lung cancer such as small cell lung cancer, non-small cell lung cancer, squamous cell lung carcinoma, small cell lung carcinoma, adenocarcinoma of the lung, large cell lung carcinoma, adeno-squamous lung carcinoma, carcinoid tumor of the lung, broncheal gland tumor or (malignant) mesothelioma. An overview over tumors of the respiratory tract may be found in Colby TV, et al.: Tumors of the Lower Respiratory Tract, Atlas of Tumor Pathology, Third Series, Fascicle 13, AFIP: Washington 1995," which shall be incorporated herein by reference.

Tumors of the urinary system may comprise bladder cancer, cancer of the kidney, renal pelvis, cancer of the ureters and cancer of the urethra, etc. Tumors of the reproductive system may comprise cancer and precursory stages thereof of the ovary, the uterus, the testis, the prostate, the epididymis, etc.

The methods of the present invention may in one embodiment be applied to breast cancer. Brest cancer may comprise any kind of carcinoma of the breast comprising e.g. any kind of ductal carcinoma (e.g. intraductal carcinoma in situ, invasive ductal carcinoma, medullary, mucinous (colloid), papillary, scirrhous or tubular ductal carcinoma), any kind of lobular carcinoma such as lobular carcinoma in situ, invasive lobular carcinoma with predominant in situ component, invasive lobular carcinoma, any kin dof nipple carcinoma (e.g. paget disease with [invasive] ductal carcinoma) and also atypical breast cancers such as phyllodes tumors and angiosarcoma.

In certain embodiments the tumors to which the method according to the present invention may be applied comprise any tumor characterized by overexpression of cyclin-dependent kinase inhibitor gene products such as e.g. $p16^{INK4a}$; or $p14^{ARF}$.

In certain further embodiments the methods of the invention are applicable to HPV associated tumors. The invention in this respect is applicable to tumors associated with HPV and especially high risk HPV types and mucosal HPV types. The high risk HPV may comprise HPV subtypes such as e.g. HPV 16, 18, 31, 33, 35, 39, 45, 51, 52, 56, 58, 59, 66 and 68. Markers for HPV infection may e.g. comprise HPV expression products of HPV genes L1, L2, E2, E4, E5, E6 or E7.

The expression "tissue or cell sample" comprises any tissue or cell samples of any kind and nature. Examples of such tissue or cell samples are secretions, swabs, lavages, body fluids, semen, cell- and tissue-samples, blood, smears, sputum, urine, stool, liquor cerebrospinalis, bile, gastrointestinal secretions, lymph, bone marrow, aspirates and biopsies of organs such as needle or punch biopsies and (fine)-needle aspirates. The samples may in certain embodiments comprise cervical smears, nipple aspirate fluid, bronchioalveolar lavages etc. In particular, smears, swabs and biopsies are indicated when the detection of anogenital cancers, e.g. cervical cancers, is concerned. According to the present invention cell or tissue samples may as the case may be comprise cells of the anogenital tract, of the respiratory tract or of the skin and its appendages. In certain embodiments the cells may be cells of the uterine cervix, the vagina, the vulva, the penis, the anus, the rectum, the breast, the bronchic tree, the lung, the peritoneum, the peritoneal space, the naso-pharyngeal space, the oral cavity or the skin. In certain embodiments of the present invention the samples may comprise cells infected by papilloma virus.

The term "biopsies" as used throughout this text shall comprise all kind of biopsies known to those of skill in the art. Thus biopsies as used in the context of the present invention may comprise e.g. resection samples of tumors, tissue samples prepared by endoscopic means or punch- or needle-biopsies of organs. Biopsies comprises specimens obtained by several different methods such as cold knife biopsies, LEEP (loop electrocautery excisional procedure) biopsies, etc.

Tissue or cell samples as used in the context of the present invention may comprise fixed or preserved cell or tissue samples. Tissue samples may comprise standard samples as used for histology such as e.g. frozen tissue, fixed tissue, paraffin embedded tissue blocks which may be fixed by an appropriate method such as e.g. formalin fixation or any other method known to those of skill in the art. Cell or tissue samples may e.g. be preserved in a standard sample collection, storage or transportation medium, known to those of skill in the art such as e.g. commercially available preservation media (formalin solution, Cytyc "PreservCyt" or "CytoLyt", Digene "Universal Collection Medium", Tripath Imaging "Cytorich", etc.). In one embodiment of the invention the cell or tissue samples provided in standard sample collection media are liquid based cytology samples (LBC samples) which are prepared according to or analogous to the methods employed for cytological LBC methods known to those of skill in the art. Suitable cell preservation media may contain a mixture of one or more selected from a group comprising alcohols, aldehydes, ketones, acids, metal-ions or sublimates, ethers etc. for preservation of cellular components. Alcohols include methanol, ethanol, (n- or i-) propanol, (n-, i- or t-) butanol or higher branched or unbranched alcohols. Aldehydes include formaldehyde, acetaldehyde, glutaraldehyde, etc. Ketones such as Acetone may be used. Acids for use in standard sample media include organic acids (acetic acid, trichloro-acetic acid, salicylic acid, picric acid) or inorganic acids such as e.g. chromic acid. Standard sample solutions may comprise metals such as silver, copper, chromium, mercury, osmium, uranium. Solutions of salts such as uranylacetate, potassiumbichromate, ammonium sulfate, etc. may be components of preservative media.

Cells preserved in suitable media (alcohols etc.) or fixed tissue samples may be used as raw samples in the methods according to the present invention. In one embodiment, the tissue or cell sample may e.g. comprise a sputum sample, a cervical swab, a nipple aspirate fluid, an oral swab, an urethral swab or the like that has been transferred to a preservative medium containing alcohol.

In certain special embodiments of the present invention the sample may be prepared as a monolayer or thin layer preparation of a cytological specimen. The respective methods for preparation of monolayer or thin-layer preparation in cytology are known to those of skill in the art. In one embodiment the preparation may e.g. comprise the ThinPrep technology. Other methods comprise conventional smears, or method employing suspensions of cells for preparation of the cytological specimens.

Preparation of a sample may comprise e.g. obtaining a sample of a tissue, of a body fluid, of cells from a patient. According to the present invention preparation of the sample may also comprise several steps of further preparations of the sample, such as preparation of dissections, preparation of cell suspensions, spreading or applying the cells to be examined onto microscopic slides, preparation of tissue arrays, isolation of polypeptides or nucleic acids, preparation of solid phase fixed peptides or nucleic acids or preparation of beads, membranes or slides to which the molecules to be determined are coupled covalently or non-covalently.

In certain embodiments of the present invention the method may be performed in an automated manner. The automation of the method may be achieved by automated staining and analysis of histological or cytological specimens on a solid surface by microscopic means. In another embodiment the automation may comprise a flow-cytometric analysis of the staining of cells in solution.

The term "overexpression" in all its grammatical forms as used in the present invention shall refer to an expression of a particular gene product at a level that is elevated compared to the level of expression in normal non-diseased cells. The term "expression" in all its grammatical forms as used in the present invention shall refer to expression of a gene product at a level that is detectable and need not be altered compared to the expression level in normal non-diseased cells.

The method for detection of the overexpression of the cyclin-dependent kinase inhibitor gene products and of expression of the cell proliferation marker gene products according to the present invention is any method, which may (but need not) be e.g. suited to detect even very small amounts of specific biological molecules in biological samples. The detection reaction according to the present invention is a detection either on the level of nucleic acids or on the level of polypeptides.

A marker molecule is said to be detectable as used in the context of the present invention, provided the marker may be detected in the course of suitable detection procedure such as e.g. in-situ-hybridization, immuno-chemical staining, hybrid capture assay etc. The level of expression of a marker molecule may be made detectable using suitable reporter reactions such as e.g. a chromogenic or fluorescence based immuno-chemical staining or in-situ-hybridization procedure for microscopic or automated analysis. Suitable methods for enhancing the reporter signal known to those of skill in the art may be applied in the course of a method according to the present invention. Thus the marker is said to be detectable in a case where the staining supersedes the respective background staining inherently obtained in the immuno-chemical staining procedure so as to produce significant staining results.

The marker molecules may be detected using reagents that specifically recognise these molecules. The detection reaction for the cyclin-dependent kinase inhibitor gene products and/or the proliferation marker gene products may comprise one or more reactions with detecting agents either recognising the initial marker molecules or recognising the prior molecules used to recognise other molecules.

In certain embodiments of the present invention two or more probes may be used for the detection of one single marker molecule. For example two or more different binding agents (e.g. antibodies) or oligonucleotide probes directed against one single marker molecule (as the case may be against different epitopes or different sequences) may be used in the course of the method as disclosed herein.

The detection of the different gene products may be performed in one reaction vessel or containment or in different containments simultaneously or subsequently in time. Thus the different gene products may be detected simultaneously in one cell co-expressing both products. Otherwise cells co-expressing the gene products may be used for separated detection reaction (separated in space or in time) to detect each a single marker in the cells. In another embodiment there might be cells expressing one or the other marker. The detection of the marker molecules in the different cells may as well be performed simultaneously or separately in time and/or space.

The detection reaction further may comprise a reporter reaction indicating the presence or absence and/or the level of the marker molecule gene products. The reporter reaction may be for example a reaction producing a coloured compound, a bioluminescence reaction, a fluorescence reaction, generally a radiation emitting reaction etc.

In certain embodiments, different marker molecules may be recognised by agents that produce different reporter signals, so that the signals referring to marker molecules could be distinguished. In one preferred embodiment of the invention the detection of the expression of one of the two or more INK4a gene products and/or proliferation marker gene products is carried out simultaneously. In this case the reporter reaction may for example employ different fluorescent or chromogenic labels for the different molecules detected.

However within the context of the present invention it must not necessarily be answered whether the one or the other proliferation marker or cyclin-dependent kinase inhibitor gene product is expressed in the cells. In certain embodiments the question is whether any proliferation marker and/or cyclin-dependent kinase inhibitor gene product is expressed. Such in the course of the experiments a procedure may be chosen, that gives the same fluorescence or chromogenic signal as indication of the presence of a proliferation marker. This procedure is suitable to improve sensitivity of the detection of the cell proliferation characteristics (different markers characteristic for active cell proliferation). As the case may be the procedure may be applied as to render one detectable signal for two, three, four or even more marker molecules being characteristic for cell proliferation. Analogous the same may under certain circumstances be true for the cyclin-dependent kinase inhibitor gene products. It must be understood, that as the case may be different staining signals for different proliferation marker molecules may be desirable. The procedures may be applied to the necessities of the respective experiment.

In certain embodiments of the present invention a combination of one or more (e.g. two different) cyclin-dependent kinase inhibitor gene products may be detected with a combination of one or more e.g. a set of two, a set of three, a set of four, a set of five or a set of even more markers for cells proliferation. As the case may be the detection of the marker molecules for cell proliferation may render only one reporter signal. In other cases each single marker for cell proliferation may render a specific reporter signal or groups of marker molecules may render specific reporter signals.

Signals for the indication of the presence of immuno-reactivity may be chromogenic signals produced by various methods known in the art. Such methods may for example comprise the generation of coloured precipitates at the site of antigen using horseradish peroxidase for enzymatic conversion and DAB, AEC, HistoMark® ORANGE, HistoMark® BLACK, etc. as a chromogen, or using the alkaline phosphatase enzyme for conversion of a chromogen and e.g. BCIP-NBT, Fast Red, New Fuchsin, etc. as chromogen. Alternatively or even in combination fluorescent signals may be used. Suitable reporter signals comprise fluorescent labels such as fluorescein, rhodamin etc.

Applicable formats for the detection reaction according to the present invention may be, blotting techniques, such as Western-Blot, Southern-blot, Northern-blot, immuno-cytochemical or immuno-histochemical procedures. The blotting techniques are known to those of ordinary skill in the art and may be performed for example as electro-blots, semidry-blots, vacuum-blots or dot-blots. Immuno-cyto/histochemical staining procedures are known to those of skill in the art and may comprise binding agent mediated detection of polypeptides as well as in situ hybridisation techniques. Both different techniques may even be applied simultaneously. In certain embodiment hybrid capture of nucleic acids may be used for the detection. Amplification reaction may also be applicable for the detection of e.g. nucleic acid molecules.

In one embodiment of the invention the detection of the level of cyclin-dependent kinase inhibitor and/or proliferation marker gene products is carried out by detection of the respective nucleic acids (e.g. mRNA) or fragments thereof present in the sample. The means for detection of nucleic acid molecules are known to those skilled in the art. The procedure for the detection of nucleic acids can for example be carried out by a binding reaction of the molecule to be detected to complementary nucleic acid probes, proteins with binding specificity for the nucleic acids or any other entities specifically recognising and binding to said nucleic acids. In one embodiment in situ hybridisation of oligonucleotide probes to nucleic acids in a sample may be used for the detection of expression products or markers.

Probes as used in the context of the present invention may be any agent binding specifically to a molecule and shall include nucleic acid probes, peptide and protein probes and other probes. In the case of nucleic acids a probe may be an oligonucleotide hybridising to a particular sequence. In one embodiment the probe may be e.g. a primer. In the case of the detection of polypeptides or proteins the probe as used herein may be e.g. a binding agent such as an antibody. In certain embodiments of the present invention the probes may be detectably labelled. The label may be selected from the group comprising a radioisotope, a bioluminescent compound, a chemiluminescent compound, a fluorescent compound, a metal chelate, or an enzyme. Probes may be applied in any detection procedure known in the art e.g. in the course of an in situ hybridisation procedure, in the course of hybrid capture assays, in the course of immuno-chemical staining reaction, in the course of blotting techniques etc.

This method may be performed as well in vitro as directly in situ for example in the course of a detecting staining reaction. Another way of detecting the marker mRNAs in a sample performed in the method according to the present invention is an amplification reaction of nucleic acids, which can be carried out in a quantitative manner such as for example the polymerase chain reaction. In a preferred embodiment of the present invention real time RT PCR may be used to quantify the level of marker mRNAs in samples of dysplasias or tumors (cells or tissue samples).

In another preferred embodiment of the invention the detection of the level of cyclin-dependent kinase inhibitor and/or proliferation marker gene products is carried out by determining the level of expression of a protein or fragments thereof. The determination of the marker gene product on the protein level can for example be carried out in a reaction comprising a binding agent specific for the detection of the particular marker polypeptide.

The binding agents can be used in many different detection techniques for example in western-blot, ELISA or immuno-precipitation. Generally polypeptide binding agent based detection can be carried out as well in vitro as directly in situ for example in the course of an immuno-chemical staining reaction. Immunochemical staining reaction may, as the case may be, be applied in histological and cytological staining procedures. Any other method for determining the amount of particular polypeptides in biological samples can be used according to the present invention.

The immuno-cytochemical (comprising inter alia histology and cytology applications) staining and/or imaging procedures for use in the context of the present invention may comprise e.g. the staining of cytological or histological preparations with chromogenic or fluorescent dyes. The staining may e.g. comprise binding of the molecules to be detected by a first binding agent, which itself is detected by a secondary binding agent, which may be labelled. The first binding agent may in certain embodiments be a nucleic acid or a protein binding agent (e.g. an antibody) and the secondary binding agent may be e.g. a secondary antibody recognizing the first binding agent.

Any methods known in the art for performing staining of cytochemical or histochemical staining may be applied in the course of a method according to the present invention.

According to the present invention binding agents may be used isolated or in combination. By means of combination it is possible to achieve a higher degree of sensitivity. The term antibody, preferably, relates to antibodies which consist essentially of pooled monoclonal antibodies with different epitopic specificities, as well as distinct monoclonal antibody preparations. Polyclonal antibody preparations may be used alternatively according to the present invention.

Binding agents as used in the context of the present invention for the detection of the level of cyclin-dependent kinase inhibitor polypeptides such as p16$^{INK4a}$ or p14$^{ARF}$ polypeptides and proliferation marker polypeptides such as e.g. MCM5, MCM2, Ki67, Ki-S5, PCNA or Ki-S2 polypeptides may comprise antibodies. An antibody or antigen-binding agent is said to react specifically, if it reacts at a detectable level with a protein disclosed herein, and does not significantly react with other proteins. The term "antibody" in all its grammatical forms as used in the context of the present invention shall comprise any kind of antibody including monoclonal and polyclonal antibodies, antigen-binding fragments, antibody fragments, fab' fragments, bi-functional hybrid antibodies, single chain antibodies, humanized antibodies peptidomimetics containing minimal antigen-binding epitopes, anti-cullines (anti-Caline™) etc.

Monoclonal antibodies are raised against antigen containing fragments of the polypeptide of the invention using any of a variety of techniques known to those of ordinary skill in the art; see, e.g., Harlow and Lane, Antibodies: A Laboratory Manual, Cold Spring Harbor Laboratory, 1988. In one such technique, an immunogen comprising the antigenic polypeptide or a synthetic part thereof is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

The cyclin-dependent kinase inhibitor gene products and/or proliferation marker gene products may according to the present invention be detected simultaneously. In this context simultaneously according to the present invention shall mean either literally at the same instant or within the same testing procedure, whereby the single detection steps are temporarily consecutive.

The detection procedure according to the present invention may furthermore comprise a cytochemical staining procedure rendering a chromogenic or fluorescent staining of cells or cell compartments. Such staining procedures are known to those of skill in the art and may for example comprise e.g. staining for acidophilic or basophilic structures, of subcellular regions (e.g. the nucleus, the mitochondria, the golgi, the cytoplasm etc.), of specific molecules (of chromosomes, of lipids, of glycoproteins, of polysaccharids etc.) in the cytological specimens. Fluorescence dyes such as DAPI, Quinacrin, Chromomycin, etc. may be employed. Furthermore chromogenic dyes such as Azan, Acridin-orange, Hematoxylin, Eosin, Sudan-red, Thiazin-stains (Toluidin-blue, Thionin) may be applied. In other embodiments staining procedures such as Pap-staining, Giemsa-staining, Hematoxylin-Eosin staining, van-Gieson staining, Schiff-staining (using Schiff reagent), staining procedures employing precipitation of metals (such as e.g. of silver in staining procedures employing Silver Nitrate) or insoluble stains such as e.g. of Turnbulls-blue (or other insoluble metal cyanides), etc. may be used in the course of a method as disclosed herein. It must be understood, that the named dyes and staining methods shall be examples for the applicable methods and that any other method known in the art may be applied to a method as disclosed herein.

The staining procedures may produce chromogenic stains for light microscopic inspection or fluorescent stains for inspection under fluorescence microscopic conditions. In another embodiment of the present invention radiation emitting procedures, procedures employing substances impairing the transmission of radiation or other contrast media for imaging of the cytological conditions in a sample (e.g. the generation of optical impression by means such as (micro-) autoradiographic or (micro-)radiographic picture generation) may be of use for a method according to the present invention.

All the staining and imaging procedures may be used for analysis not only in microscopic procedures but also in automated analysis procedures such flow cytometry, automated microscopic (computerized or computer aided) analysis or any other method for analysis of stained cytological specimens.

The analysis of the staining or imaging results of the different procedures may be performed in a single analysis step or in different subsequent steps. E.g. the light microscopic inspection of a specimen may be performed before or after fluorescence microsopic inspection of the specimen. In Fluorescence microscopy the analysis of different stains with different excitation wavelengths may be analyses simultaneous or subsequently. Other imaging methods may be employed simultaneously or subsequently to the named procedures.

There may be various circumstances, under which combinations of different staining methods will be suitable. E.g. in cases, where no satisfying cytological staining results may be achieved by immuno-chemical staining the additional application of general cytological staining techniques may be suitable.

Analysis of staining results according to the present invention in certain embodiments of the invention comprises the detection of certain staining patterns in histological procedures. Generally staining patterns can be classified in various ways. Any suitable classification of staining patterns in histology shall be applicable for the purpose of the present invention. Especially the detection of diffuse staining pattern shall be of relevance for the invention. A "diffuse staining pattern" refers to a histological staining of an epithelium where immunochemical staining for a particular gene product is detected as a continuous staining of cells of the basal and parabasal cell layers of the squamous cervical epithelium, with or without staining of cells of superficial cell layers. In certain embodiments the detection of diffuse staining pattern for cyclin-dependent kinase inhibitors may be the basis for prediction of progression risk or of potential for aggressive growth of tumors. Diffuse staining pattern is to be discriminated from focal staining patterns, where only staining of isolated cells or small cell clusters; i.e., a non-continuous staining, particularly not of the basal and parabasal cells is observed.

Preparations as used in the context of the present invention shall refer to a chemical preparation comprising more than one substance. In particular the preparations of the present invention are preparations comprising at least two different probes one of them being specific for a cyclin-dependent kinase inhibitor gene product at least one other of them being specific for a cell proliferation marker gene product. In addition the preparation according to the present invention may comprise further substances such as preservatives, stabilizers, buffers, diluents, and others. The substances used and the compositions suitable for providing probes are known to those of skill in the art. In certain embodiments of the present invention the probes may be nucleic acid probes or antibodies. Polyclonal and/or monoclonal antibodies for incorporation into the preparation of the invention may be derived from any suitable animal known to those of skill in the art including without limitation mouse, rat, hamster, goat, rabbit, human, horse, cow, pig, etc. Also synthetic or genetically engineered antibodies or antibodies generated in transgenic plants, microorganisms or animal may be incorporated. In certain embodiments of the invention the probes may be monoclonal antibodies. In further embodiments the antibodies may be chosen in a way that the antibodies specific for cyclin-dependent kinase inhibitors are derived from one animal (e.g. mouse, rat or the like) and the antibodies specific for cell proliferation marker are chosen from another animal (e.g. goat, rabbit etc.)

In one embodiment the preparation may for example be a preparation of $p16^{INK4a}$ specific antibodies together with Ki67 specific antibodies.

The present invention provides methods for predicting the potential for aggressive growth and the risk to progress to high grade cancer for tumors comprising determining in a cell based detection procedure based on the detection of the presence of overexpression of cyclin-dependent kinase inhibitor gene products. In certain embodiments of the invention also the detection of specific staining patterns of overexpression in immuno-histochemistry may be applied in this method. Further the present invention provides methods for predicting the potential for aggressive growth and the risk to progress to high grade cancer for tumors comprising determining in a cell based detection procedure performed on the basis of the detection of the simultaneous presence of overexpression of at least one cyclin-dependent kinase inhibitor gene product and the expression of at least one cell proliferation marker gene product in at least one single cell. Even further the present invention provides preparations of probes for diagnosis namely for predicting the progression risk and/or the potential for aggressive growth of tumors. The invention solves the problem present in the art that well suited tools for prognosis of growth characteristics and of the progression risk of tumors were not sufficiently available. The present invention now puts the skilled person in the position to predict prognosis and the potential for aggressive growth. The methods and preparations of the present invention accordingly may form the basis for improvement in patient care and in tailoring adequate therapy for patients.

EXAMPLES

The following examples are given for the purpose of illustration only and are not intended to limit the scope of the invention disclosed herein.

Example 1

Prediction of the Progression Risk of Histological Specimens Obtained from the Cervix Uteri Classified as CIN 1 by Detection of $p16^{INK4a}$ Protein and Ki67 Protein Archival histological samples (sections generated from neutral buffered formalin fixed, paraffin embedded punch biopsies) of the cervix uteri were immuno-histochemically stained using antibodies specific for $p16^{INK4a}$ and Ki-67. In total 10 specimens have been stained. Specimens with available follow up data have been chosen. For 6 specimens follow up examinations revealed regression of the CIN 1. For 4 specimens follow up examinations revealed progression of the CIN1 lesions to high grade dysplastic lesions. For all 10 specimens also HPV data were available or were generated during the experiments performed.

All specimens were treated as follows.

Tissue blocks were sectioned into slices of 4 μm thickness. Prior to deparaffinization slides have been placed in a drying oven at a temperature of 60° C. for a time period of 30 minutes to melt the paraffin. Tissue slides have then been de-paraffinized to remove embedding medium have been rehydrated before the staining procedure was be performed. Subsequently Epitope retrieval was performed for 10 minutes at 98° C. using 10 mM Tris as Epitope Retrieval Solution. Staining of the slides has been performed with a mixture of primary antibodies, i.e. monoclonal mouse-anti-human-$p16^{INK4a}$ and monoclonal rabbit-anti-human-Ki67. For detection secondary reagents based on a polymeric support coupled to the respective secondary antibodies and to alkaline phoshpatase (for the anti-rabbit secondary antibody) and to horseradish peroxidase (for the anti-mouse secondary antibody) have been used. The staining was performed on a Labvision Autostainer Instrument using the following program:

200 μL Peroxidase-Blocking Reagent—5 minutes;
200 μL Primary Antibody Solution—30 minutes;
200 μL Visualization Reagent HRP—15 minutes;
200 μL Visualization Reagent AP—15 minutes;
200 μL Substrate-Chromogen Solution (DAB)—10 minutes;
200 μL Substrate-Fast Red (Fast Red)—15 minutes;

Between and after the single steps appropriate rinse steps were performed. After staining counterstain with hematoxylin was performed and slides were permanently mounted.

Figure 2:
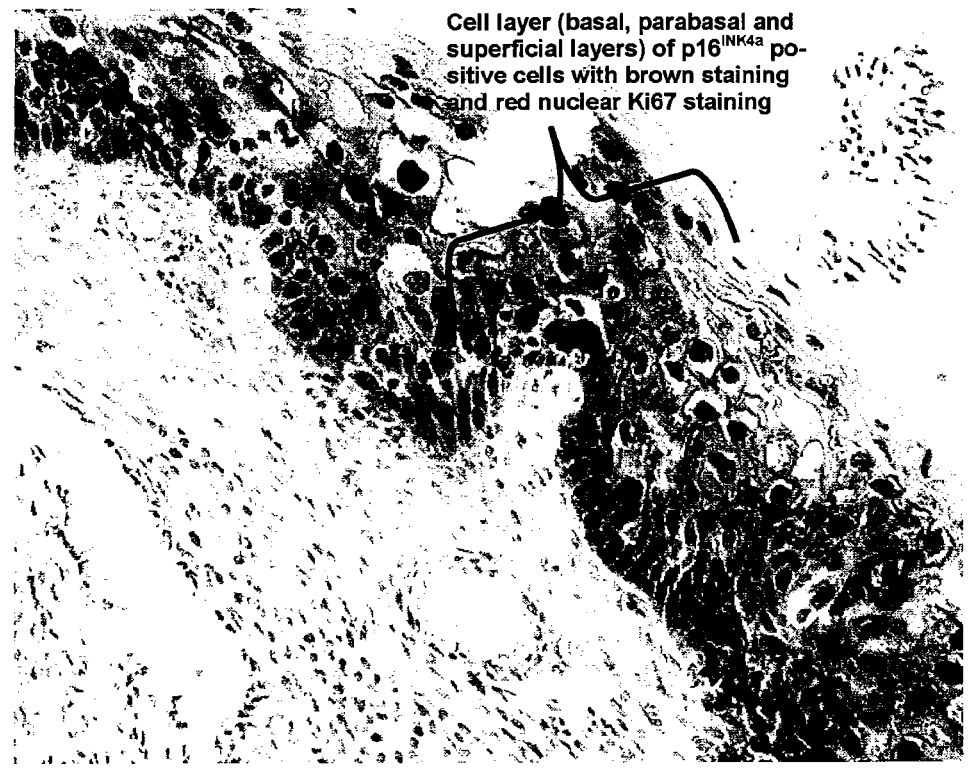
FIG. 2: Photomicrograph of a biopsy specimen from the cervix uteri immuno-histochemically double-stained using monoclonal antibodies directed to human $p16^{INK4a}$ protein and human Ki67 protein. Ki67 rendered specific red staining, $p16^{INK4a}$ specific brown staining. The staining pattern is diffuse for $p16^{INK4a}$. Many cells double-stained for both markers are present.

Photomicrographs of the slides are given in FIGS. 1 to 2.

Microscopic inspection of the slides revealed that those CIN 1 lesions that had proven to regress spontaneously showed no cells double-stained for $p16^{INK4a}$ and Ki67 (cf. FIG. 1). Further these lesions showed sporadic or focal staining pattern for $p16^{INK4a}$ and no diffuse staining pattern (cf. also FIG. 1).

A correlation between high risk HPV results and p16 staining in immuno-histochemistry and $p16^{INK4a}$/Ki67 double staining in immuno-histochemistry for CIN that showed spontaneous regression is given in the following tables:

TABLE 1

Correlation of $p16^{INK4a}$ staining results with hr HPV status for CIN1 lesions that had proven to spontaneously regress.

|  | p16 (+) | p16 (−) | Σ |
|---|---|---|---|
| hr HPV+ | 1 | 4 | 5 |
| hr HPV− | — | 1 | 1 |
| Σ | 1 | 5 | 6 |

TABLE 2

Correlation of p16/Ki67 double-staining results with hr HPV status for CIN1 lesions that had proven to spontaneously regress.

|  | P16/Ki67 (+) | p16/Ki67 (−) | Σ |
|---|---|---|---|
| hr HPV+ | — | 5 | 5 |
| hr HPV− | — | 1 | 1 |
| Σ | — | 6 | 6 |

$p16^{INK4a}$ is considered positive (+) for the purpose of the above tables once there is a positive $p16^{INK4a}$ immuno-reactivity irrespective of the staining pattern observed. $p16^{INK4a}$ and Ki67 double staining is considered positive (+) in case there is at least one single cell observed in the specimen that is positive for both markers and accordingly is double-stained.

In contrast all of the four lesions that had proven to progress to high grade lesions show double-staining for $p16^{INK4a}$ and Ki67 in at least one single cell in the specimen. Furthermore such specimens showed strong diffuse staining pattern for $p16^{INK4a}$ alone (cf. FIG. 2).

A correlation between high risk HPV results and $p16^{INK4a}$ staining in immuno-histochemistry and $p16^{INK4a}$/Ki67 double staining in immuno-histochemistry CIN1 with progression potential is given in the following tables:

TABLE 3

Correlation of $p16^{INK4a}$ staining results with hr HPV status for CIN1 lesions that had proven to progress to high grade lesions.

|  | P16 (+) | P16 (−) | Σ |
|---|---|---|---|
| hr HPV+ | 4 | — | 4 |
| hr HPV− | — | — | — |
| Σ | 4 | — | 4 |

TABLE 4

Correlation of p16/Ki67 double-staining results with hr HPV status for CIN1 lesions that had proven to progress to high grade lesions.

|  | p16/Ki67 (+) | p16/Ki67 (−) | Σ |
|---|---|---|---|
| hr HPV+ | 4 | — | 4 |
| hr HPV− | — | — | — |
| Σ | 4 | — | 4 |

Again p16$^{INK4a}$ is considered positive (+) for the purpose of the above tables once there is a positive p16$^{INK4a}$ immunoreactivity irrespective of the staining pattern observed. p16$^{INK4a}$ and Ki67 double staining is considered positive (+) in case there is at least one single cell observed in the specimen that is positive for both markers and accordingly is double-stained.

It could be concluded, that as on the basis of the p16$^{INK4a}$ staining pattern prediction of the progression risk of CIN 1 lesions would have been facilitated. However it must be noted, that the interpretation of the staining pattern of histological preparation leaves room for subjective interpretation and is therefore to somewhat extent prone to errors. As an alternative that is less prone to subjective interpretation the double staining method is provided. Also in this case on the basis of the presence of cells double-stained for p16$^{INK4a}$ and Ki67 it would have been possible to predict those CIN 1 lesions tested that had the potential to progress to high grade lesions. For hr HPV test the results show that 9 out of 10 tested specimens were hr HPV positive. So 5 out of 6 of the specimens which spontaneously regressed showed hr HPV positivity.

The experiment shows that determination of the progression risk of CIN1 lesions was possible on the basis either of p16$^{INK4a}$ staining pattern (diffuse staining pattern is indicative of a risk to progress to high grade lesions), on the basis of double staining of cells for p16$^{INK4a}$ and Ki67 or on a combination of hr HPV with p16$^{INK4a}$ positivity. For the double staining the prediction of the risk for progression is also given when combining the double staining test with hr HPV testing.

Example 2

Prediction of the Progression Risk in Breast Biopsies by Detection of p16$^{INK4a}$ Protein and Different Cell Proliferation Marker Proteins In total 15 archival biopsy specimens of breast tumors (ductal carcinoma in-situ and lobular carcinoma in situ specimens) were used for the present experiment. 10 of the tested specimens were of less aggressive tumors, 5 stem from more aggressive tumor types. Progression risk and aggressiveness of the tumors were proven by follow up data on the individual cases. For each sample five sections were subjected to different double staining experiments. In each experiment p16$^{INK4a}$ staining was combined with one of the following cell proliferation markers: Ki67, MCM2, KiS2, MCM5, topoisomerase-2-alpha.

Specimen preparation and staining was performed as described above for Example 1.

Also in this experiment microscopic inspection revealed, that double-staining of single cells was detected only in those specimens that had more aggressive characteristics and had unfavourable prognosis. The five specimens characterized by the more aggressive growth as proven by follow up data showed diffuse staining pattern for p16$^{INK4a}$ and in addition also are characterized by many double stained cells showing Ki67 staining together with p16$^{INK4a}$ staining in single cells. For the other double staining experiments each of the tested cell proliferation markers showed in at least 4 out of the 5 specimens at least one single cell with double staining. A combination of any of the tested cell proliferation markers with p16$^{INK4a}$ accordingly is suited to detect those tumors of the breast that have the potential for aggressive growth that need more rigorous therapy. To enhance the sensitivity for double staining a combination of more than one proliferation marker could be considered to be included in combination with the cyclin dependent kinase inhibitor.

For the specimens where follow up had proven less aggressive growth properties and more favourable prognosis p16 overexpression could be shown as well. However the staining pattern was not diffuse here. Further staining for p16$^{INK4a}$ and for the proliferation markers could be detected in the overall specimen however not as a double staining of a single cell.

Accordingly as well the staining pattern for the cyclin dependent kinase inhibitor as well as the double staining of single cells with both markers is indicative for the more aggressive growth properties.

The invention claimed is:

1. A method for predicting a potential for tumors of the urinary system for aggressive growth and/or a risk to progress to high grade cancer from low grade cancer, comprising:
    obtaining a tumor sample from the urinary system of a subject;
    measuring by a cell based detection procedure whether at least one single cell of the sample simultaneously overexpresses p16INK4a and expresses Ki67; and
    determining that the tumors have a potential for aggressive growth and/or a risk to progress to high grade cancer when there is at least one single cell in the sample having the simultaneous presence of overexpression of p16INK4a and the expression of Ki67.

2. The method of claim 1, wherein the cell based detection procedure is immunohistochemistry or immunocytochemistry.

3. The method of claim 1, wherein the tumor is bladder cancer.

4. The method of claim 1, said measuring uses antibodies against p16INK4a and Ki67.

5. The method of claim 1, wherein the sample is a tissue sample or a cell sample.

* * * * *